(12) United States Patent
Stewart et al.

(10) Patent No.: US 6,447,119 B1
(45) Date of Patent: Sep. 10, 2002

(54) APPARATUS FOR VISUALIZING THE EYE'S TEAR FILM

(75) Inventors: Jeffrey L. Stewart, Greenwich, CT (US); Robert K. Maloney, Pacific Palisades, CA (US); Bruce E. Truax, Southington, CT (US)

(73) Assignee: Visionrx, Inc., Elmsford, NY (US)

( * ) Notice: Subject to any disclaimer, the term of this patent is extended or adjusted under 35 U.S.C. 154(b) by 0 days.

(21) Appl. No.: 09/498,803

(22) Filed: Feb. 7, 2000

Related U.S. Application Data

(63) Continuation-in-part of application No. 08/910,194, filed on Aug. 4, 1997, now Pat. No. 6,059,773, which is a continuation-in-part of application No. 08/695,616, filed on Aug. 12, 1996, now Pat. No. 5,873,832.

(51) Int. Cl.$^7$ ................................................ A61B 3/10
(52) U.S. Cl. ...................................................... 351/212
(58) Field of Search ................................. 351/200, 205, 351/206, 208, 211, 212, 221, 246, 247; 606/4, 5

(56) References Cited

U.S. PATENT DOCUMENTS

| | | | | |
|---|---|---|---|---|
| 5,110,200 A | * | 5/1992 | Snook | 351/212 |
| 6,213,605 B1 | * | 4/2001 | D'Souza et al. | 351/212 |

* cited by examiner

Primary Examiner—George Manuel
(74) Attorney, Agent, or Firm—J. De La Rosa

(57) ABSTRACT

A technique for evaluating the topography of a cornea is disclosed, which utilizes a virtual image/object of a keratoscope pattern. The disclosed topography system includes a structured light source to create the keratoscope pattern or another diagnostic pattern, an optical assembly to focus the created pattern upon or behind the cornea, and for capturing the image reflected off the patient's eye and directing the reflected image toward an imaging system for processing. Light emitted by the light source is preferably not in the visible range, to minimize discomfort to the patient. Since the topography is evaluated with a projected virtual image, there is no nose or brow shadow, thereby allowing better corneal coverage. The optical system includes an aperture stop which is preferably conjugate with a point behind the corneal surface approximating the center of a normal cornea. Thus, wide angle capture is achieved as reflected rays reaching the imaging system appear as if they originated at the center of the cornea. A pupil detection mechanism is disclosed which is performed independently of the diagnostic pattern illumination, thereby facilitating pupil detection. In an alternate embodiment, the diagnostic pattern is generated using a variable light pattern generator, which provides flexibility in selecting target images to achieve various diagnostic abilities. The disclosed topography system may be used as a visual field measuring device, a perimeter, or an instrument for visualizing abnormalities in the eye's tear film.

21 Claims, 14 Drawing Sheets

APPARATUS FOR VISUALIZING THE EYE'S TEAR FILM

CROSS-REFERENCE TO RELATED APPLICATION

This is a continuation-in-part of U.S. patent application Ser. No. 08/910,494, filed Aug. 4, 1997 now U.S. Pat. No. 6,059,773, which in turn is a continuation-in-part of U.S. patent application Ser. No. 08/695,616, filed Aug. 12, 1996, issued as U.S. Pat. No. 5,873,832, each of which is incorporated herein by reference.

FIELD OF THE INVENTION

The present invention relates to a device for evaluating the curvature or shape of the cornea of the eye, and more particularly, to a corneal measurement device that assists with pre-operative or post-operative measurements of the cornea, with contact lens fitting and with the diagnosis of diseases of the cornea. Additionally, the present invention relates to an ophthalmic instrument for visualizing disruptions in the eye's tear film which covers the cornea.

BACKGROUND OF THE INVENTION

The cornea, being the front surface of the eye, provides its major refracting surface and is important to quality vision. Recently, a number of corneal surgical techniques have been developed for correcting visual deficiencies, such as near-sightedness, far-sightedness and astigmatism. In order to assist with such surgical techniques, a number of devices have been proposed or developed to evaluate the topography, i.e., the shape or curvature, of the cornea. In addition, such corneal topography techniques are useful for fitting contact lenses and for the diagnosis and management of corneal pathologic conditions, such as keratoconus and other ectasias. For example, prior to performing a corneal surgical technique to correct a refractive error, the patient is preferably screened using a corneal topography device to rule out the possibility of subclinical keratoconus.

Corneal topography is typically measured using a series of concentric lighted rings, known as a keratoscope pattern 5, shown in FIG. 1. In one typical embodiment, shown in FIG. 2, keratoscope pattern 5 is created by a keratoscope target 10, consisting of illuminated concentric rings which emit light rays which are projected onto the cornea of a patient's eye 15. Light rays 12, 20 are reflected off patient's cornea 15, and a portion of light ray 20 is captured by an objective lens 25 and focused onto an imaging system 30, such as a video camera. A computer 35 is utilized to compare the image captured on imaging system 30 with a stored reference pattern, or other known information, to identify any distortions in the captured image and thus calculate any deformations in the patient's cornea.

While conventional corneal topography devices have achieved significant success, such devices suffer from a number of limitations, which, if overcome, could significantly enhance their accuracy and utility. In particular, earlier designs for topography devices have incorporated large keratoscope targets, causing the overall size of the prior art devices to be quite large. In an operating room or a doctor's office, however, where space is at a premium, it is desirable to minimize the overall size of the topography device.

In addition, commercially available topography devices, such as the design illustrated in FIG. 2, typically measure the topography of only a relatively small area of the cornea. For example, in the design shown in FIG. 2, the light beam is emitted from a large, flat, backlit keratoscope target 10 and is then reflected off cornea 15. Thereafter, a portion of light 20 reflected off cornea 15 is focused by small objective lens 25 at the center of keratoscope target 10 onto imaging system 30, such as a CCD chip. Additional light rays 12 reflected from the peripheral portions of cornea 15, however, are not captured by objective lens 25 and are therefore not imaged onto imaging system 30. Therefore, such prior art devices are unable to measure the peripheral cornea.

To overcome this problem, prior art devices have attempted to capture the light rays reflected from the peripheral portions of cornea 15 by designing a keratoscope target 10' in the shape of a cylinder or cone, as shown in FIG. 3, encompassing the peripheral cornea. In this manner, light rays emitted by cylindrical or conical keratoscope target 10' will form a pattern 5 of illuminated rings which will be reflected off cornea 15. The reflected light rays, including light rays reflected off the peripheral portions of cornea 15, will be captured by objective lens 25 and imaged onto imaging system 30. To be effective, however, cylindrical or conical keratoscope target 10' must be positioned very close to the eye, and thereby tends to impinge on the patient's brow and nose. In addition to being potentially uncomfortable and potentially contributing to the spread of disease, the close approach of keratoscope target 10' makes the design very error-prone, as a slight error in alignment or focusing causes a large percentage change in the position of the keratoscope rings relative to the eye.

In addition, current systems tend to provide poor pupil detection and do not accurately measure non-rotationally symmetric corneas, such as those with astigmatism. The location of the pupil is particularly important in planning surgical procedures for correcting visual deficiencies. In current systems, pupils are typically detected by deciphering the border of the pupil from the image of the keratoscope rings. This is particularly difficult with conventional designs, however, as the intensity transition from the black pupil to a dark iris is minimal compared to the intensity transition from a bright keratoscope ring image to a dark interring spacing. As a result, the pupil detection algorithms in current systems often fail.

Furthermore, current systems have difficulty detecting the edges of the keratoscope rings and difficulty separating ring images from background iris detail. Conventional corneal topography systems image the iris along with the keratoscope rings, as know as "mires". Particularly in patients having light-colored irises, however, the bright reflection from iris detail obscures the rings, thereby making detection of ring edges difficult. Finally, conventional devices utilize high intensity visible light to illuminate the keratoscope target and therefore cause discomfort to the patient. The high intensity light is required because relatively little light is actually reflected from the cornea and captured by the measuring devices.

As is apparent from the above discussion, a need exists for a more compact corneal topography device. Another need exists for a topography system that allows a large area of corneal coverage without the focusing problems and invasive approach of previous designs. A further need exists for a system incorporating improved pupil detection by using an image that does not include the keratoscope rings. Yet another need exists for a topography device providing improved separation of the corneal reflection of the keratoscope pattern from the iris detail. A further need exists for a topography system utilizing light levels that are not unpleasant for the subject undergoing measurement. An additional need exists for a topography device that permits accurate measurement of non-rotationally symmetric corneas, such as those with astigmatism.

SUMMARY OF THE INVENTION

Generally, according to aspects of the present invention, a method and apparatus for measuring the topography of the cornea are provided. The method and apparatus utilize a virtual image of a keratoscope pattern or other diagnostic pattern, which is projected at a desired distance in front of the patient's eye. Since the topography is evaluated with a virtual image, there is no nose or brow shadow, allowing better coverage of the cornea and providing a design which is relatively insensitive to focusing errors.

In certain embodiments, however, it has been found preferable to position the image of the keratoscope pattern at some other location. For example, a virtual object of the keratoscope pattern may be formed just behind the cornea such that after being reflected from the surface of the cornea is re-imaged just in front thereof. Likewise, however, distortions in the cornea are observed in the reflected real image of the keratoscope pattern.

The disclosed topography system includes a structured light source, preferably consisting of an illumination source and a beam modulating system, to create the keratoscope pattern or other desired diagnostic pattern. In order to minimize discomfort to the patient, light emitted by the illumination source is preferably not in the visible range. In addition, the illumination source is preferably monochromatic.

In accordance with an aspect of the present invention, the beam modulating system may be embodied as a photographic slide film consisting of opaque markings on a transparent background, or a variable light pattern generator, such as an array of liquid crystal pixels, or an array of light emitting diodes. In this manner, the beam modulating system can provide flexibility in selecting pattern images to achieve various diagnostic abilities.

An optical assembly focuses the created pattern upon the cornea, and thereafter captures the image reflected off the patient's eye and directs the reflected image toward an imaging system, such as a CCD, for processing. According to a feature of the invention, the optical assembly preferably includes means for preventing scattered light reflected from the patient's iris from being imaged by the CCD. In one embodiment, a pair of polarizing filters having the same polarization attenuate the scattered light reflected from the patient's iris, thereby permitting a clean image of the keratoscope pattern, as reflected off the patient's cornea, on the CCD camera.

According to a further feature of the invention, the optical system achieves wide angle capture by including an aperture stop which is preferably conjugate with a point behind the corneal surface approximating the center of curvature of a normal cornea. Thus, reflected rays reaching the imaging system appear as if they originated at the center of curvature of the cornea.

Furthermore, the optical system may also be used for observing disruptions or abnormalities in the eye's tear film by observing localized changes in the intensity of the acquired image of the cornea.

The corneal topography device preferably includes a centration illumination source and a focusing laser which are utilized to center and focus the corneal topography system relative to the patient's cornea. During the centration and focusing operation, the structured light source used to generate the diagnostic pattern is preferably not illuminated. Thus, pupil detection is facilitated, since the pupil boundaries are not obscured by one or more rings of the keratoscope pattern.

In accordance with a further aspect of the invention, a method of calibrating the corneal topography device is disclosed. The method comprises the steps of: positioning a calibration sphere approximating the size of a cornea at a desired focal point; illuminating the calibration sphere with a diagnostic pattern; creating a first image on an imaging system of a reflection of the diagnostic pattern off the sphere; positioning a cursor on the imaging system at approximately the center of the first image; creating a second image on the imaging system of a reflection of a centration illumination source off the sphere; adjusting the position of the centration illumination source so that the second image is approximately centered around the previously positioned cursor; and storing the first image as a reference image for calculating topographical information about an unknown cornea.

Yet another aspect of the invention allows the disclosed topography system to be reconfigured as a perimeter to evaluate a patient's field of vision. When configured as a perimeter, the structured light source is preferably embodied as a backlit liquid crystal array, a cathode ray tube or an array of light emitting diodes. To measure the patient's visual field, the patient observes a virtual image of the pattern produced by the structured light source, which is projected at a distance in front of the patient's eye. In addition, an infrared laser illuminates the patient's pupil with an infrared beam. A reflection of the infrared beam scattered off the patient's iris is imaged on the CCD.

According to a further feature of the invention, the optical system includes means for attenuating light which is reflected off the patient's cornea during the visual field measurement, such as a pair of perpendicular polarizers positioned in the optical path. The system monitors fixation by tracking the movement of the pupil, using the scattered infrared image. When the center of the pupil moves beyond a predefined threshold, an alarm indicates when fixation is lost.

BRIEF DESCRIPTION OF THE DRAWINGS

A more complete understanding of the present invention, as well as further features and advantages of the invention, will be obtained by reference to the detailed description and drawings.

DETAILED DESCRIPTION

Figure 1:
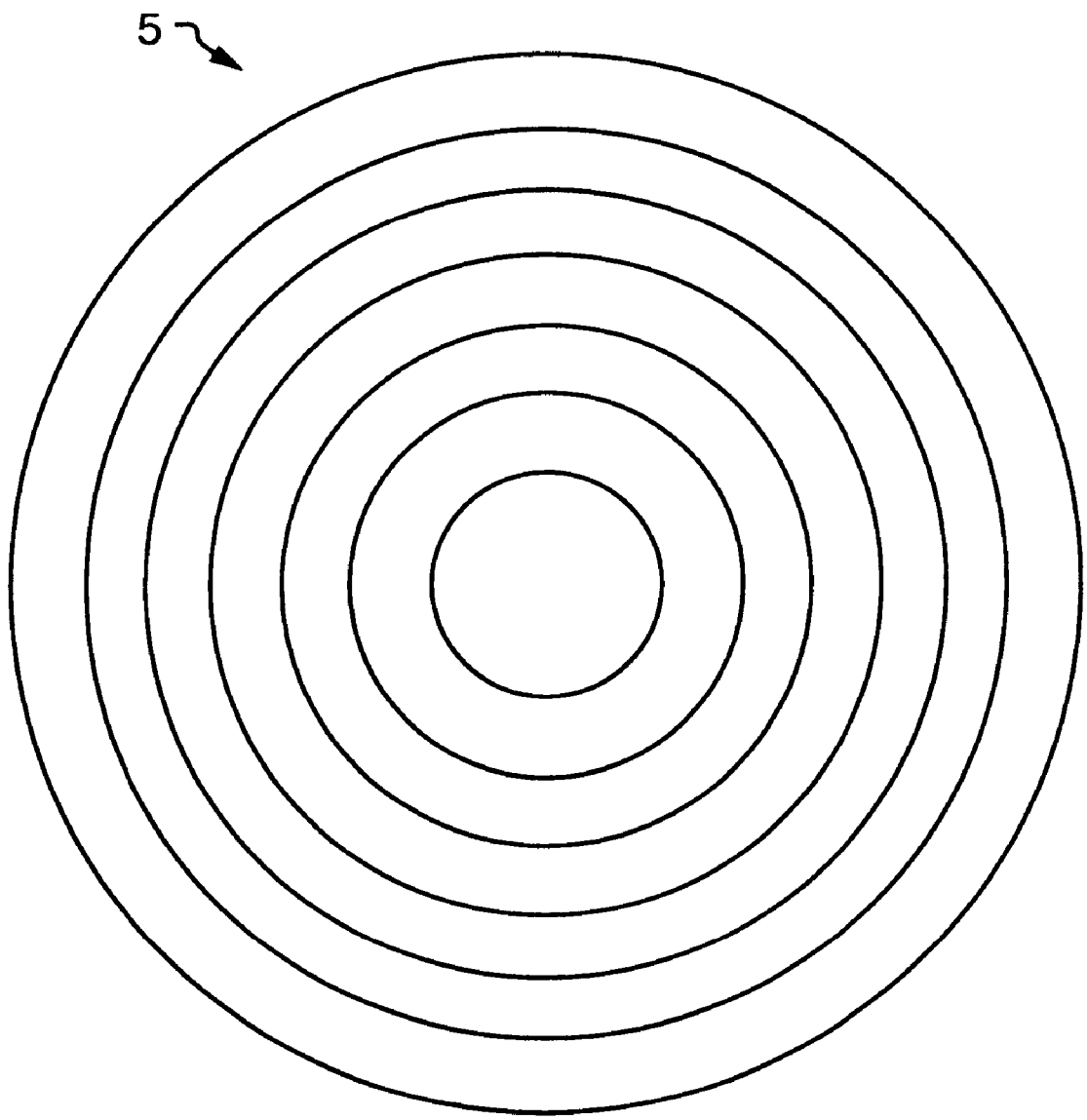
FIG. 1 is a diagram illustrating a keratoscope pattern of the prior art.
Figure 4:
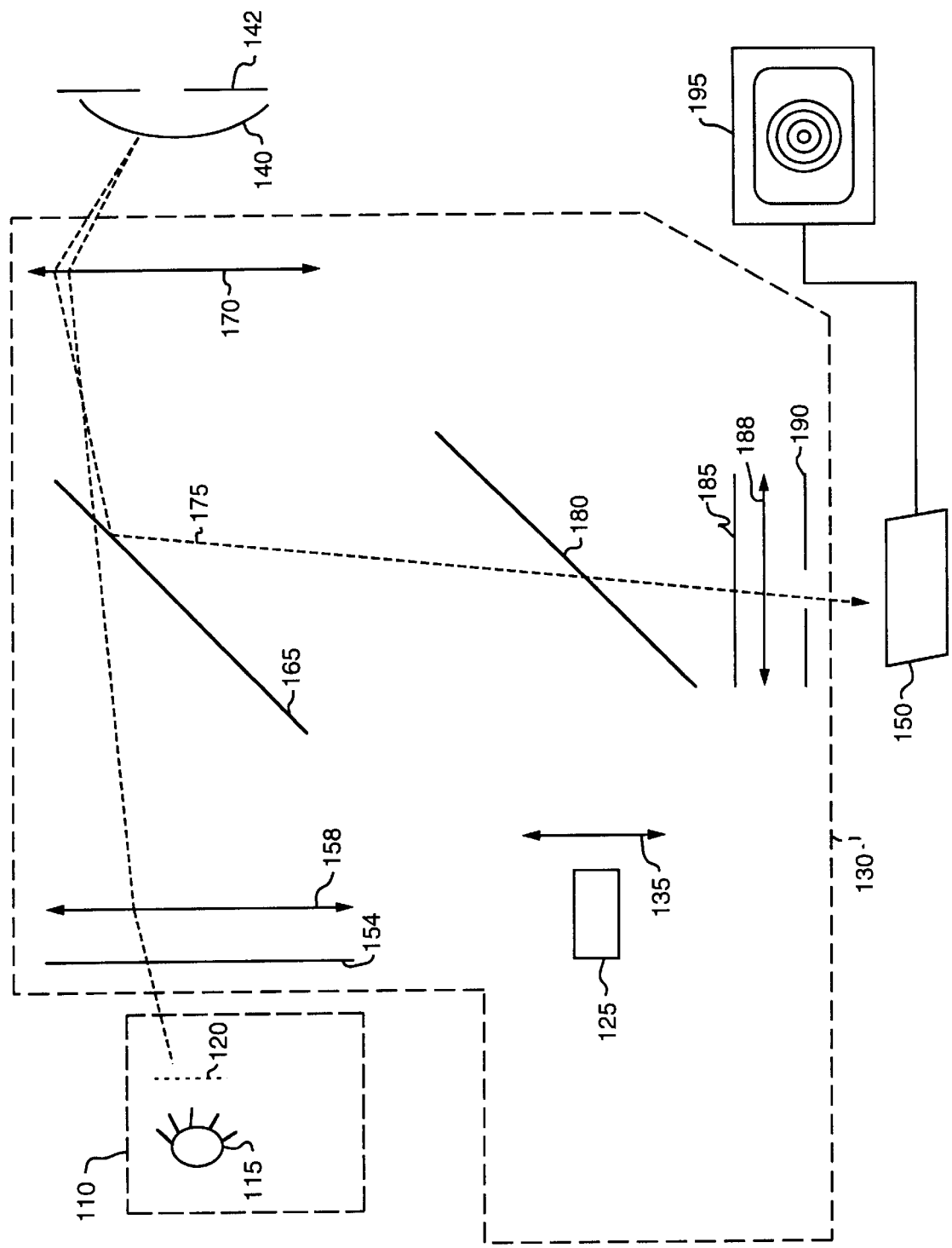
FIG. 4 is a block diagram of a corneal topography device incorporating features of the present invention.

As shown in FIG. 4, a corneal topography device according to the present invention includes a structured light source 110, for creating a diagnostic pattern, such as keratoscope pattern 5 (FIG. 1), and an optical assembly 130 for focusing the created pattern 5 upon cornea 140 of a patient's eye and for capturing the pattern reflected off the patient's eye and directing the reflected pattern toward an imaging system 150, such as a CCD chip or other imaging sensor, including CMOS devices, for further processing. Structured light source 110 preferably consists of an illumination source 115 and a beam modulating system 120 for creating keratoscope pattern 5, as illustrated in FIG. 1, or an alternate pattern as discussed below. In one embodiment, structured light source 110 includes a diffuser to spread out the light.

According to one feature of the invention, light emitted from illumination source 115 is preferably not in the visible range, thereby minimizing the discomfort to the patient resulting from the high intensity source. In one embodiment, beam modulating system 120 for creating keratoscope pattern 5 is embodied as photographic slide film consisting of opaque markings on a transparent background.

As shown in FIG. 4, optical assembly 130 preferably includes, in sequence, a polarizing filter 154, a focusing lens 158, for capturing and directing the polarized light upon a beam splitter 165 and an objective lens 170, which focuses keratoscope pattern 5 upon cornea 140. In addition, light 175 reflected from cornea 140 is captured by objective lens 170 and is then reflected by beam splitter 165 toward a second beam splitter 180. The light passes through beam splitter 180, in a known manner, and through polarizing filter 185, which is oriented parallel to polarizing filter 154. Thereafter, the light passes through a focusing lens 188, which serves to direct the reflected pattern through an aperture stop 190, such as an adjustable round hole or an iris, and onto CCD chip 150. CCD chip 150 transmits the captured image to a personal computer 195, or another processor, where the image of the reflected pattern is displayed on a computer screen for further evaluation by an operator.

According to a further feature of the invention, polarizing filter 185, having the same polarization as polarizing filter 154, serves to prevent scattered light reflecting from the patient's iris 142 from being imaged on CCD chip 150. In this manner, scattered light reflected from patient's iris 142 is attenuated, permitting a clean image of the keratoscope pattern, as reflected off cornea 140, on the CCD camera, without noise and background detail from patient's iris 142, thereby simplifying image processing.

Figure 7:
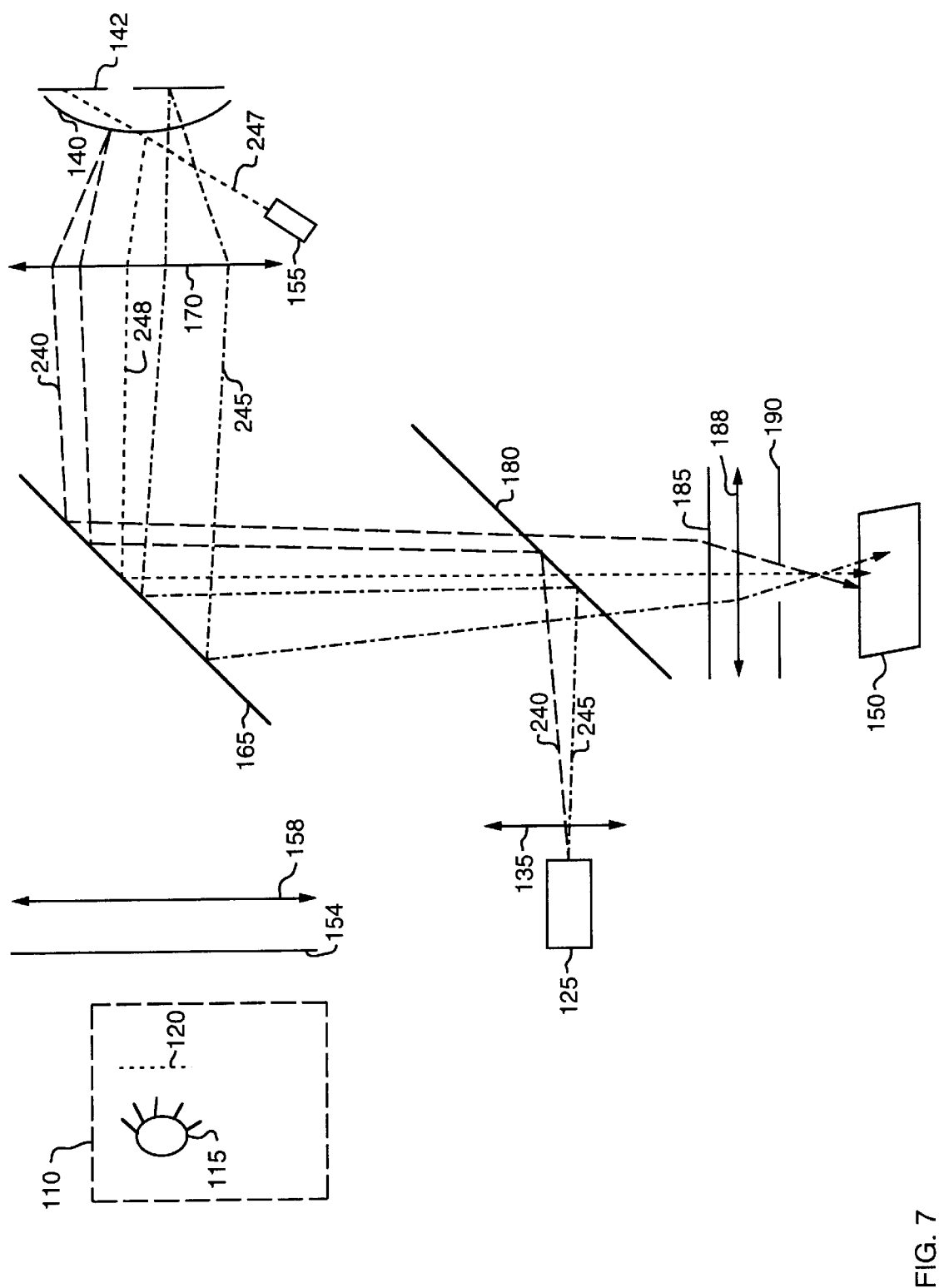
FIG. 7 illustrates the corneal topography device of FIG. 4 in operation during focusing and centration.

In addition, the corneal topography device includes a centration illumination source 125 and a collimating lens 135, and a focusing laser 155, discussed further below in conjunction with FIG. 7, which are utilized during a centration and focusing process to center and focus the corneal topography system relative to patient's cornea 140. In a further embodiment, discussed below in conjunction with FIG. 10, the topography device may be configured as a perimeter to evaluate the patient's field of vision. When configured as a perimeter, centration illumination source 125 preferably emits light in the infrared range.

Figure 5:
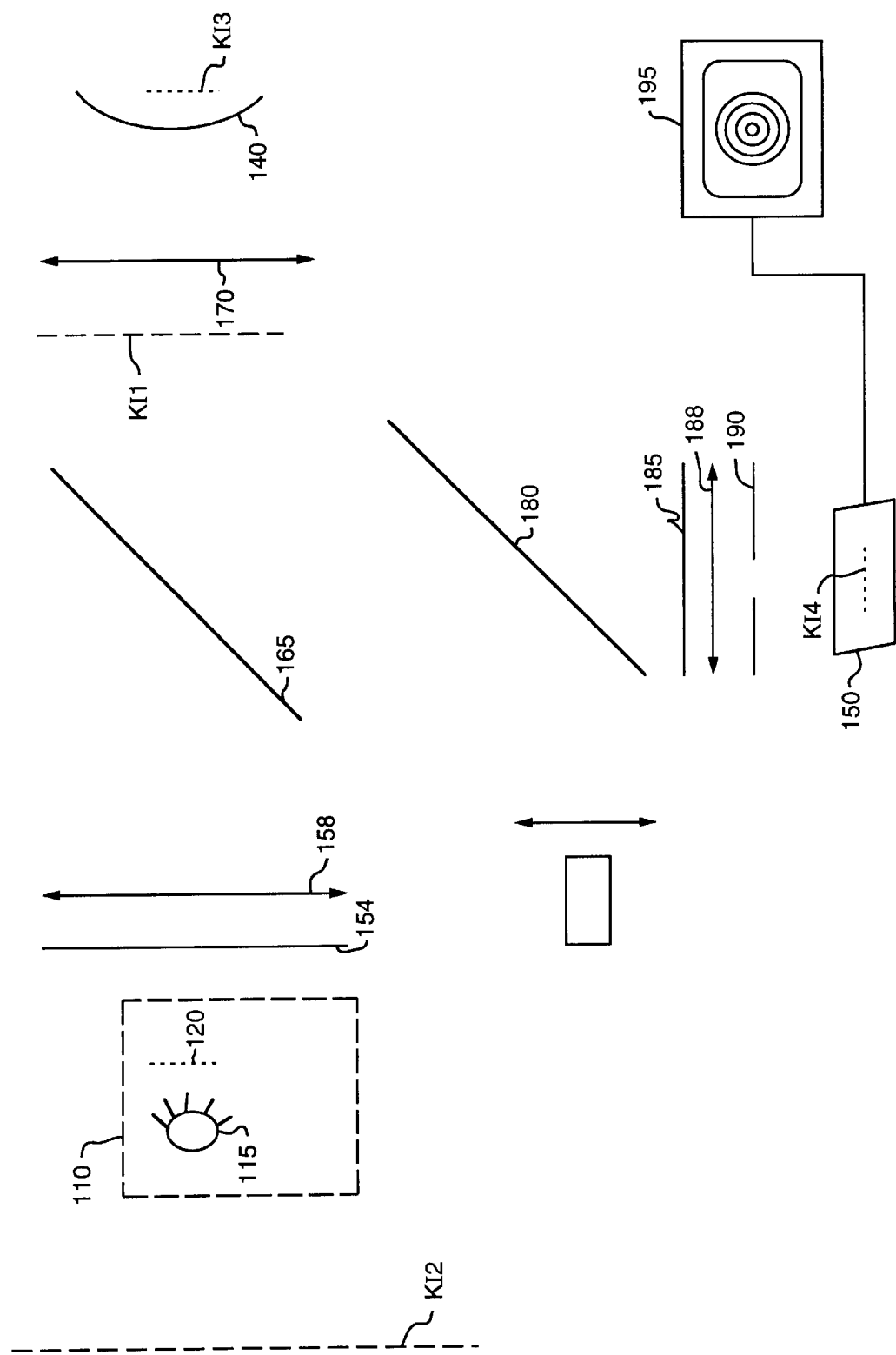
FIG. 5 illustrates the location of real and virtual images of the keratoscope pattern in the embodiment of FIG. 4.

As the light beam passes from beam modulating system 120 through the various elements of optical system 130 to CCD chip 150, several images, including real images, and virtual images and objects, of the keratoscope pattern are created, as illustrated in FIG. 5. Image KI1 is a real image of keratoscope pattern 5 created by focusing lens 158 and lying inside the focal point of objective lens 170. In a real image, all the light from a point on the pattern passing through the optical system, actually passes close to or through a point on the image. In other words, because KI1 is a real image, keratoscope pattern 5 could actually be seen on a piece of paper, if a piece of paper were inserted into the optical assembly at the location of KI1.

In addition, objective lens 170 projects image KI1 to create a virtual image KI2 of keratoscope pattern 5, preferably lying approximately 0.3 meters in front of the patient's eye and being approximately 0.4 meters in diameter. In a virtual image, rays of light only appear to diverge from a particular location, without actually being focused there. In other words, when a patient looks into objective lens 170, a virtual image KI2 of keratoscope pattern 5 appears to be emanating from the location of the virtual image.

Upon looking into objective lens 170, patient's cornea 140 will reflect the perceived virtual image KI2 and create a virtual object KI3, located approximately 4 mm behind the cornea 140 in the illustrative embodiment. Virtual object KI3 is captured by objective lens 170 and focusing lens 188, which cooperate to create a real image KI4 of the virtual object KI3 on CCD 150.

Figure 2:
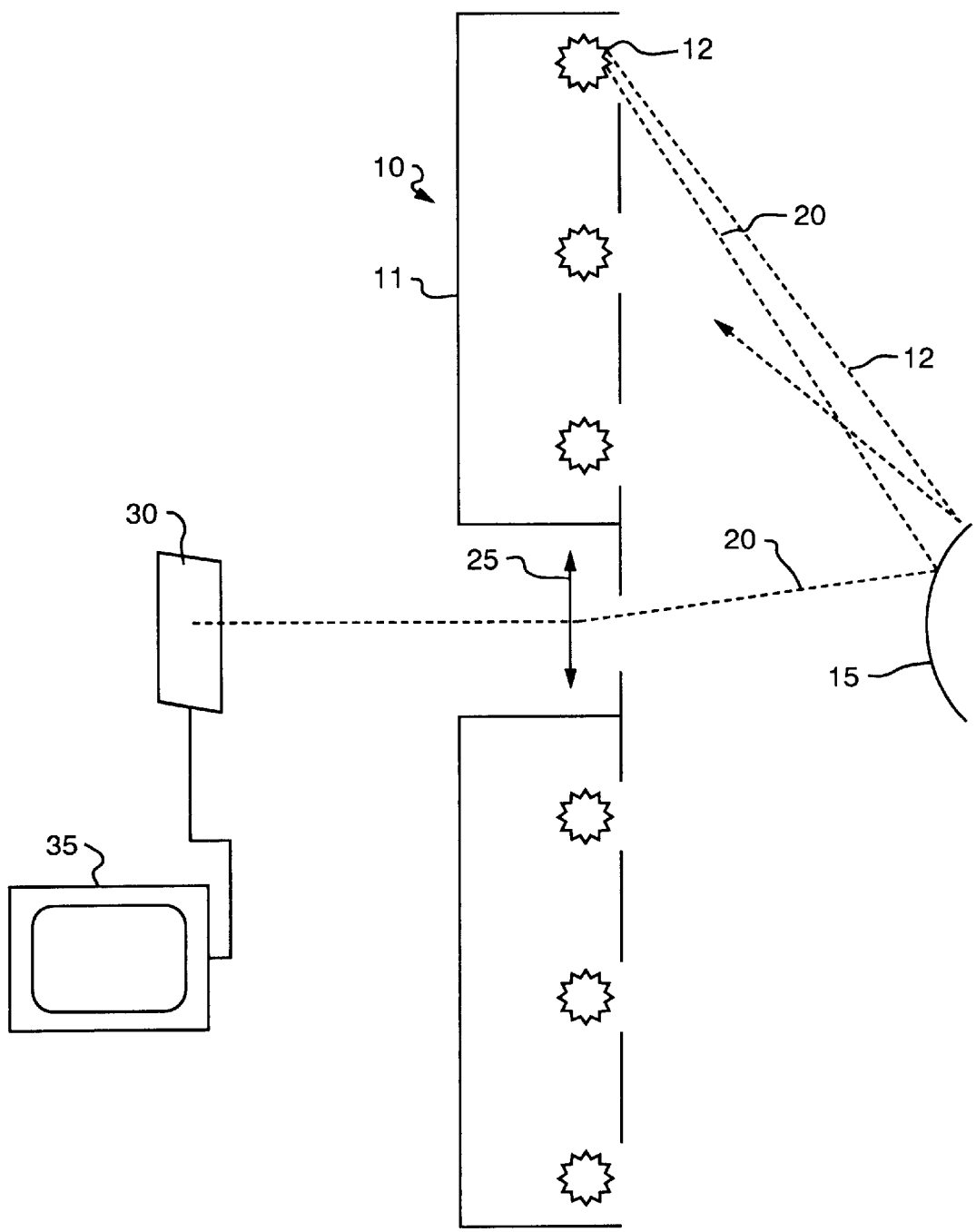
FIG. 2 is a block diagram illustrating the optical arrangement of a prior art topography device.
Figure 3:
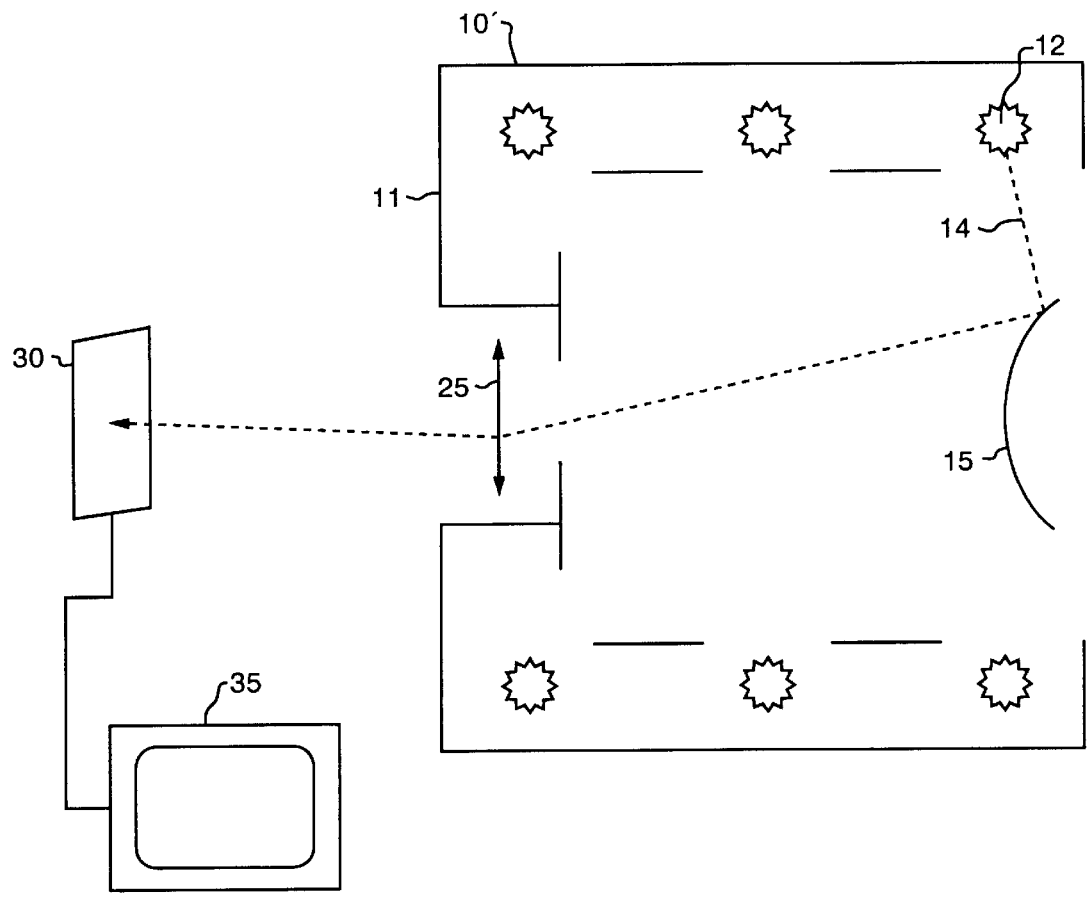
FIG. 3 is a block diagram illustrating the optical arrangement of an alternative prior art topography device design.

Thus, according to a feature of the invention, a virtual image KI2 of keratoscope pattern 5 is created at a desired distance in front of the patient's eye. Because the distant image is virtual, there is no nose or brow shadow, allowing better coverage of the cornea and providing a design which is relatively insensitive to focusing errors. It has been observed that the accuracy of the present topography system in projecting keratoscope pattern 5 on the cornea is determined by the apparent location of the virtual keratoscope image KI2, rather than by the actual location of objective lens 170 in relation to the eye. Thus, the present invention provides a design that is relatively insensitive to focusing, in a similar manner to the prior art design discussed above in conjunction with FIG. 2, as well as exhibiting improved corneal coverage, in a manner similar to the prior art design discussed above in conjunction with FIG. 3.

Figure 6:
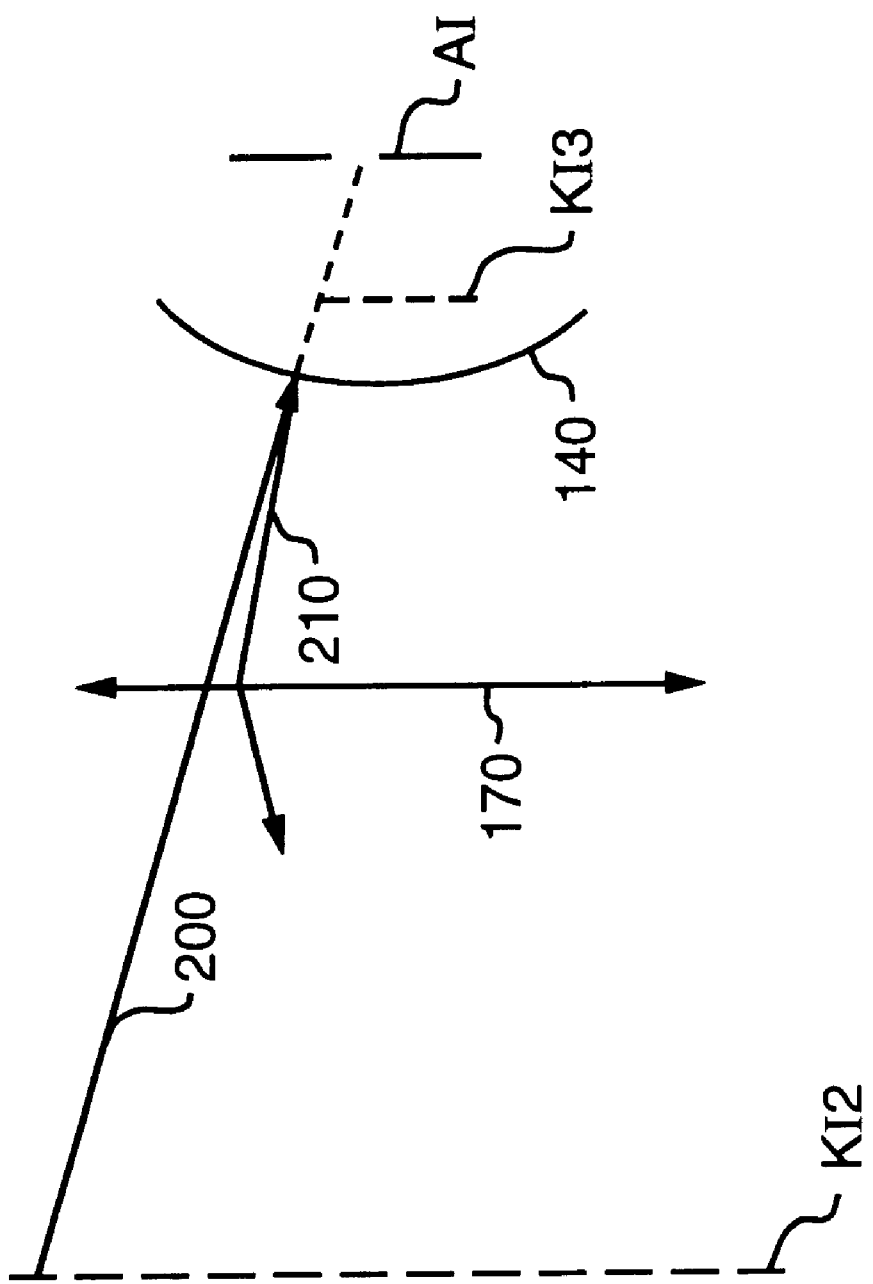
FIG. 6 is an enlarged view of a method of wide angle capture of a virtual image, according to a feature of the present invention.

According to a further feature of the invention, measurement of a large area of the cornea is facilitated by incorporating wide angle capture of reflected virtual object KI3. As shown in FIG. 6, a light ray 200 from the virtual keratoscope pattern image KI2 travels through objective lens 170 and strikes cornea 140 at an angle that is nearly perpendicular to the corneal surface. Light ray 200 is thereafter reflected back from the cornea along a path 210 nearly parallel to the incoming ray 200 from the virtual image KI2 of keratoscope pattern 5. Aperture stop 190 (FIG. 5) is preferably conjugate through objective lens 170 and focusing lens 188 with a point approximately 7.8 mm behind the corneal surface, corresponding to the center of curvature of a normal cornea, creating a virtual object AI of aperture stop 190, approximately at the center of curvature of the cornea, as shown in FIG. 6.

This optical configuration ensures that each bright region of the keratoscope pattern substantially illuminates only a corresponding region of the cornea. This is in contrast to the prior art, wherein the bright regions of the keratoscope pattern diffusely illuminate the entire cornea and iris, thereby causing a significant reduction in image contrast. In the present invention, light rays originating from each portion on the keratoscope pattern reaching the corneal surface subtend a substantially small solid angle due to the high f-number of the optical system. As such, the illumination is well controlled, thereby avoiding illuminating those regions of the iris corresponding to the dark regions of the keratoscope pattern. Advantageously, this significantly enhances the image contrast and thus the image quality.

Furthermore, this configuration also ensures that a ray that reaches CCD chip 150 was reflected nearly back along incident ray 200, as if emerging from the aperture image AI, thereby allowing a large area of corneal coverage with a target at a significant (virtual) distance from the eye. In other words, this limits reflected rays reaching CCD chip 150 to those rays that reflect as if they originated at the center of curvature of a normal cornea, creating the wide angle capture that characterizes this system. In this manner, the ray reflected off cornea 140 can be reflected at a wide angle and still be captured by the large objective lens. In an alternate embodiment (not shown), aperture stop 190 can be positioned in the optical path between focusing lens 158 and objective lens 170, but still conjugate to the center of curvature of a normal cornea through objective lens 170. In this alternate embodiment, the rays emerging from KI2 are directed toward the image AI of aperture stop 190, so wide angle capture of KI3 is still achieved.

In order to achieve the parameters associated with the illustrative embodiment, namely, so that the center of aperture stop 190 is approximately conjugate to the center of a typical cornea (having a radius of 7.8 mm), and to place the virtual image at a distance of approximately 0.3 m in front of the cornea with a diameter of approximately 0.4 m, objective lens 170 should have a diameter of approximately 5.5 cm and an f-number of approximately 0.7. In addition, objective lens 170 should be positioned approximately 2 cm from the corneal surface.

CENTRATION AND FOCUSING

In order to achieve proper centration and focus of the corneal image, the operator preferably watches a video image of the patient's eye on the computer screen while adjusting the position of the corneal topography device relative to the eye in three dimensions. As shown in FIG. 7, during the centration and focusing operation, centration illumination source 125 and focusing laser 155 are preferably simultaneously illuminated, while illumination source 115 is not illuminated. Light rays 240, 245 emitted from centration illumination source 125 pass through collimating lens 135 and reflect off beam splitter 180 and beam splitter 165. Light rays 240, 245 pass through objective lens 170 and a portion of rays 240 reflect off the cornea, while another portion of rays 245 pass through cornea 140 and are reflected off patient's iris 142.

Rays 240 reflected off the cornea are captured by objective lens 170, reflect off beam splitter 165, are transmitted by beam splitter 180 and are imaged by CCD chip 150. Rays 240 create an image on CCD 150 of centration illumination source 125 that is reflected from the patient's cornea. Meanwhile, the remaining light rays 245 which pass through cornea 140 and are reflected off patient's iris 142, are captured by objective lens 170, are reflected by beam splitter 165 and imaged onto CCD chip 150. Rays 245 thereby create an image of the subject's iris 142 and pupil on the CCD chip. Thus, during the centration process a composite image of the patient's iris, pupil and the reflection of illumination source 125 is created on the CCD chip.

The operator observes the composite image on the display and judges the degree of centration of the reflected image of illumination source 125, for example, with respect to a crosshair or other fixed reference mark on the display to ensure that the topography device is in a proper centered position relative to the patient's cornea.

Simultaneously with centration, focusing laser 155, such as a laser diode, is preferably obliquely illuminating the cornea with a laser beam 247. Most of laser beam 247 will pass through the nearly transparent cornea, and fall harmlessly against patient's iris 142. A small percentage of laser beam 247, however, will be scattered by the cornea. The scattered beam 248 is collected by objective lens 170, is reflected by beam splitter 165 and is imaged onto CCD chip 150. The operator moves the corneal topography device closer or farther from the patient's cornea to align the image of scattered beam 248 with the same reference mark used for centration. When the reflection of centration illumination source 125 and the image of focusing laser 155 are properly aligned, the operator activates a switch to measure the topography. Those skilled in the art will readily note that properly positioning the topography device is necessary to accurately determine the base radius of curvature of the cornea.

Alternatively, a portion of laser beam 247 reflected off the cornea is imaged onto a linear position detector (not shown) that generates a signal proportional to the position of the reflected beam. Of course, other position detectors may be used, such as quadature position detectors or two-dimensional position detectors. It should be understood that when the reflected beam is appropriately centered on the linear position detector, the device is designed such that the cornea is in proper focus. Otherwise, the operator moves the corneal topography device closer or a farther from the patient's cornea to center the reflected beam on the linear position detector. In the event, however, that the patient moves just before the measurement is made, the position of the reflected laser beam, which is now offset from the center, is recorded. Using triangulation which is well known in the art, any deviation in the position of the reflected laser beam is used to correct for errors in the computed base radius of curvature caused by defocusing.

In addition, the patient undergoing corneal measurement observes centration illumination source 125 during the centration process to ensure that the patient's visual axis is aligned with the optical axis of the topography device. In an alternate embodiment, the high intensity centration illumination source 125 emits nonvisible light, so as to be more comfortable for the patient, and light source 115 is simultaneously illuminated to provide a point of fixation for the patient during the measurement.

In alternate embodiments, centration illumination source 125 can be located at different positions in optical system 130, as would be apparent to a person of ordinary skill in the art. For example, beam splitter 180 can be positioned in the optical path between keratoscope target 120 and beam splitter 165, with the centration illumination source 125 introduced through relocated beam splitter 180.

Thus, according to a feature of the present invention, patient's iris 142 is diffusely illuminated by centration illumination source 125 during centration, thereby allowing easy visibility of the pupil. Further, since illumination source 115 is not illuminated in the preferred embodiment during the centration process, and thus a keratoscope pattern is not generated, the boundaries of the pupil are not obscured by one or more rings of the reflected keratoscope pattern, as with prior art devices.

TOPOGRAPHICAL MEASUREMENT

Once the operator is satisfied that the composite image has been properly centered and focused on the computer screen, the operator pushes a switch to initiate measurement of the cornea. Upon initiation of the measurement process, centration illumination source 125 and focusing laser 155 are turned off, while illumination source 115 is activated to permit measurement of the cornea. In a preferred embodiment, personal computer 195 stores at least the last two successive video frames. Thus, at the moment immediately after illumination source 115 is illuminated, the topography system has one video frame containing the pupil, diffusely illuminated, with no keratoscope image, and one video frame with the keratoscope image reflection with no obscuring detail from patient's iris 142. From the video frame containing the pupil image, the outlines of the pupil are easily detected. From the video frame containing the keratoscope image, the edges of the keratoscope pattern image are easily detected. The detected keratoscope pattern image is thereafter compared to the stored reference image to yield information about the corneal topography, in a known manner.

It should be understood that on a smooth surface the radius of curvature may be dependent on the direction the measurement was made. As such, a surface may have many different radii of curvature. There are, however, typically a maximum and a minimum radius of curvature along directions perpendicular to one another. In mathematics, the product of the maximum and minimum radii of curvature is referred to as the "Gaussian curvature."

It is contemplated that the Gaussian curvature at each point on the cornea may be calculated from the reflected keratoscope pattern, and displayed using, for example, pseudo-coloring. Such information may be useful to surgeons inasmuch as it is typically unchanged by certain surgical procedures, such as astigmatic keratotomy. Furthermore, it may be useful in analyzing the regularity and distribution of transplanted corneal tissue.

Alternatively, other mathematical derivatives of the Gaussian curvature may be used, such as the square root, or inverse of the Gaussian curvature. Similarly, various other approximations to the Gaussian curvature may be used. For example, one approximation is simply multiplying the radii of curvature taken along two perpendicular directions, such as along the sagittal and tangential directions.

CALIBRATION

To calibrate the invention, a calibration sphere (not shown) having a radius of approximately 7.8 mm, to approximate the size of a normal cornea, is positioned, for example, with a bracket that fits objective lens 170 and holds the calibration sphere at the desired focal point. Calibration proceeds in three steps. First, the operator illuminates illumination source 115 and positions a cursor on the computer screen on the middle of the captured image KI4 of keratoscope pattern 5. Next, centration illumination source 125 is illuminated, and its position is adjusted manually so its reflected image on the computer screen is centered around the cursor. Finally, the image KI4 of the reflection of keratoscope pattern 5 off the calibration sphere is stored, thereby providing the necessary reference image to calculate the topography of an unknown cornea.

The calibration process involves comparing the known reference radius to the calculated radius for each point on the computer screen. Normally, devices that rely on wide angle optics must contend with significant optical aberrations. The proposed calibration method allows neutralization of aberrations in the system. Each point on the computer screen corresponds to a chief ray emerging in a specific direction from the image of aperture stop 190 at the center of the calibration sphere. An optical aberration will appear in the calibration sphere image as a deviation of a keratoscope ring, or part of a ring, from the position that would be expected by paraxial optics. When an unknown cornea is imaged, the amount of deviation due to aberrations is unchanged, and can be removed by a subtraction process to yield an aberration-free image from which accurate corneal topography can be calculated.

STRUCTURED LIGHT SOURCE

As previously indicated, the corneal topography system includes structured light source 110 for creating a keratoscope pattern or another desired pattern. Structured light source 110 preferably includes illumination source 115 and beam modulating system 120. Illumination source 115 may be embodied as any light emitting device, including a laser source, a light emitting diode, or an incandescent lamp. The light emitted by illumination source 115, as well as by centration illumination source 125, is preferably either naturally monochromatic, as in for example light from a laser, or is made monochromatic by the use of a color filter. In this manner, chromatic aberration, which would normally be expected with the use of low f-number lenses, is minimized.

In one embodiment, previously discussed, beam modulating system 120 is embodied as a piece of photographic slide film consisting of opaque markings on a transparent background, to create the desired pattern. Depending on the application, however, it may be desirable for beam modulating system 120 to be embodied as a programmable image quality light pattern generator for creating variable patterns. In a preferred embodiment, programmable light pattern generator 120 is comprised of an array of liquid crystal pixels, capable of selectively blocking incident light in one mode, i.e., by a scattering or absorption process, and transmitting light in another mode, as is well known to those skilled in the art. In this manner, the liquid crystal array can create a desired pattern by selectively placing each individual pixel of the array in a relaxed (light blocking) state, or in an aligned (light transmitting) state, or in an intermediate state between the two extreme positions, according to a "gray scale." The pixels of the liquid crystal array are preferably selectively energized via a driver which may be controlled by computer 195.

In an alternate embodiment, structured light source 110 may be embodied as an array of light emitting diodes (LEDs), a cathode ray tube (CRT) or as a laser controlled by an X-Y galvanometer or scanner or any other light generating or transmitting display. In each of these alternate embodiments, an additional illumination source is not required. In a further, less complex, embodiment, alternate patterns can be achieved, for example, by incorporating a rotatable pattern wheel, with a plurality of selectable positions each creating a unique pattern.

ALTERNATE PATTERNS

It has been observed that by modifying the conventional keratoscope pattern, additional or more accurate information can be obtained about the corneal topography. In particular, in order to enhance detection and measurement of non-rotationally symmetric corneas, such as those with astigmatism, a keratoscope pattern which permits identification of the meridian of origin of the reflected ray is preferably utilized. If a particular cornea being evaluated is not rotationally symmetric, angularity will be introduced in the rays reflected from the cornea and the conventional assumption that the target pattern projected through the optical system does not undergo any angular displacement is violated.

Figure 8A:
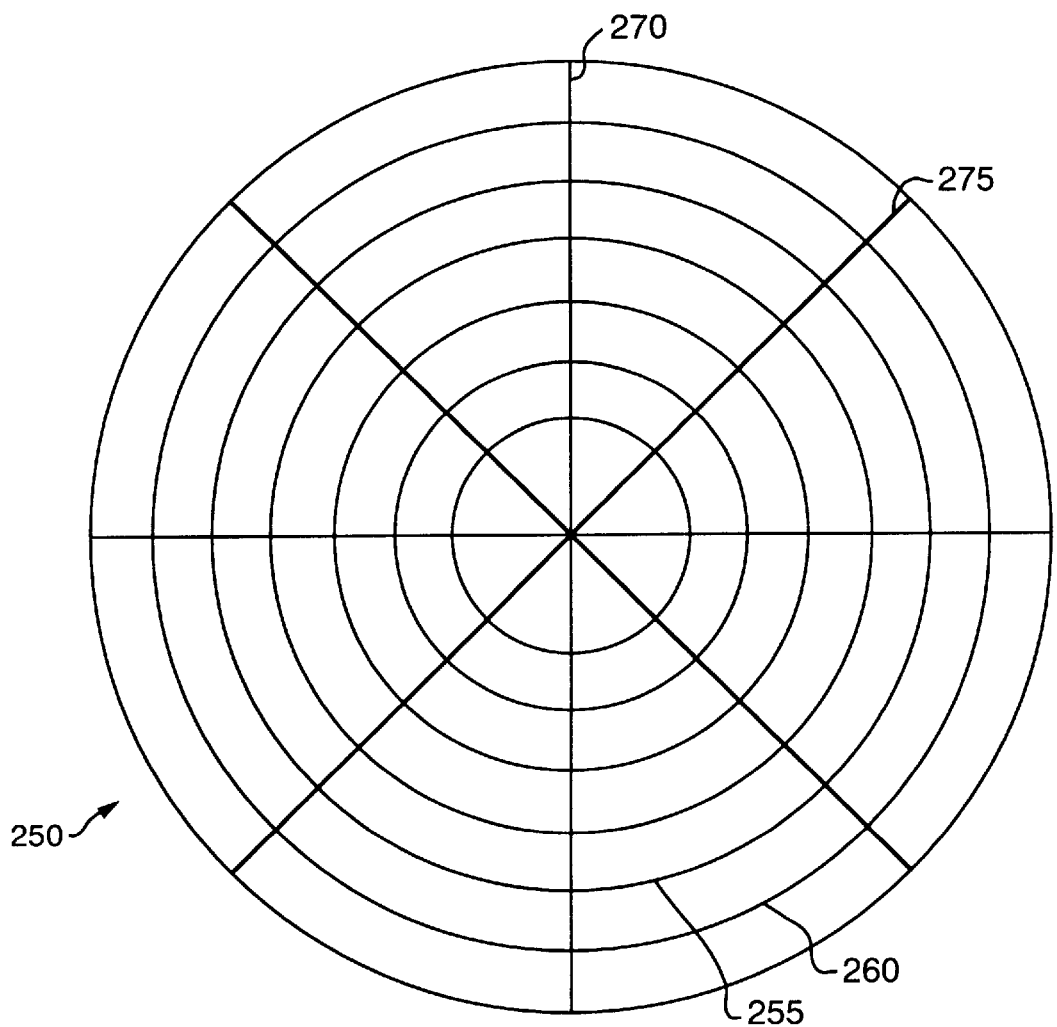
FIG. 8A illustrates an alternative keratoscope pattern for use with the present invention.

Thus, according to a further feature of the invention, an enhanced keratoscope pattern, such as pattern 250 illustrated in FIG. 8A, is utilized. Keratoscope pattern 250 of FIG. 8A consists of a plurality of concentric rings 255, 260 as well as a plurality of radial lines 270, 275. In this manner, when the pattern reflected off the patient's cornea is imaged on the CCD chip, the features on each ring allow identification of rays that leave the plane containing the system's primary axis, and the point of reflection from the cornea. By creating features on the target that differentiate segments of each ring, the problem of non-coplanarity of the prior art is solved.

Figure 8B:
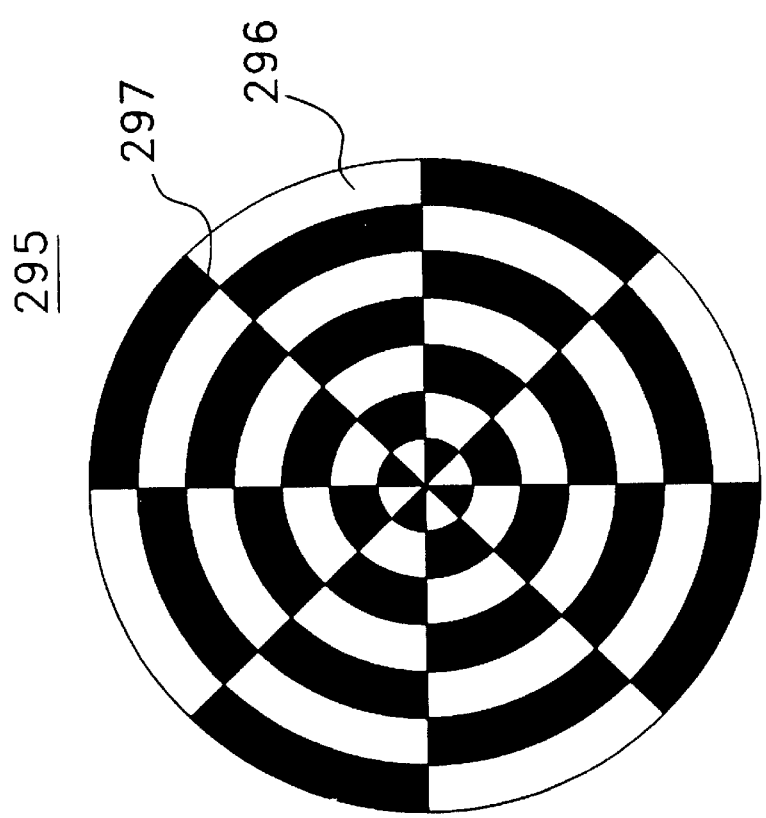
FIG. 8B illustrates another alternative keratoscope pattern for use in the present invention.

In variations of this embodiment, circumferential marks, a circular or square checkerboard pattern or a grid of perpendicular lines, for example, may be utilized instead of the radial lines 270, 275 to achieve a similar result. For example, a circular checkerboard pattern 295 may be used as illustrated in FIG. 8B. Circular checkerboard pattern 295 consists of concentric circles 296 cut across with radial lines 297 having alternating regions of light and dark. The concentric circles allow the topography to be measured in a manner well known in the art. Furthermore, the radial lines delimited by the regions of light and dark allow the system to identify the plane of origin of the incoming rays from the cornea. This is particularly useful for corneas with astigmatism. Moreover, using alternating regions of light and dark inherently defines the radial lines, reducing the line thickness to zero.

For measurement of abnormal corneas, such as highly curved or unusually flat corneas, it may be desirable to change the diameter or spacing of the concentric rings on the keratoscope target. Thus, it can be seen that when beam modulating system 120 is embodied as a programmable light pattern generator, such as a liquid crystal array, or as an easily replaceable photographic slide film, in the manner described above, the number of different patterns which can be achieved with the present invention is virtually unlimited. In this manner, the enhanced flexibility in creating patterns provided by the present invention permits greater diagnostic abilities.

In addition, the present invention permits the cornea to be initially evaluated with a generic pattern, such as pattern 5 of FIG. 1, and upon detection of certain anomalies, to be further evaluated with an alternate target which has been designed to optimize evaluation of the particular identified anomaly.

Figure 9:
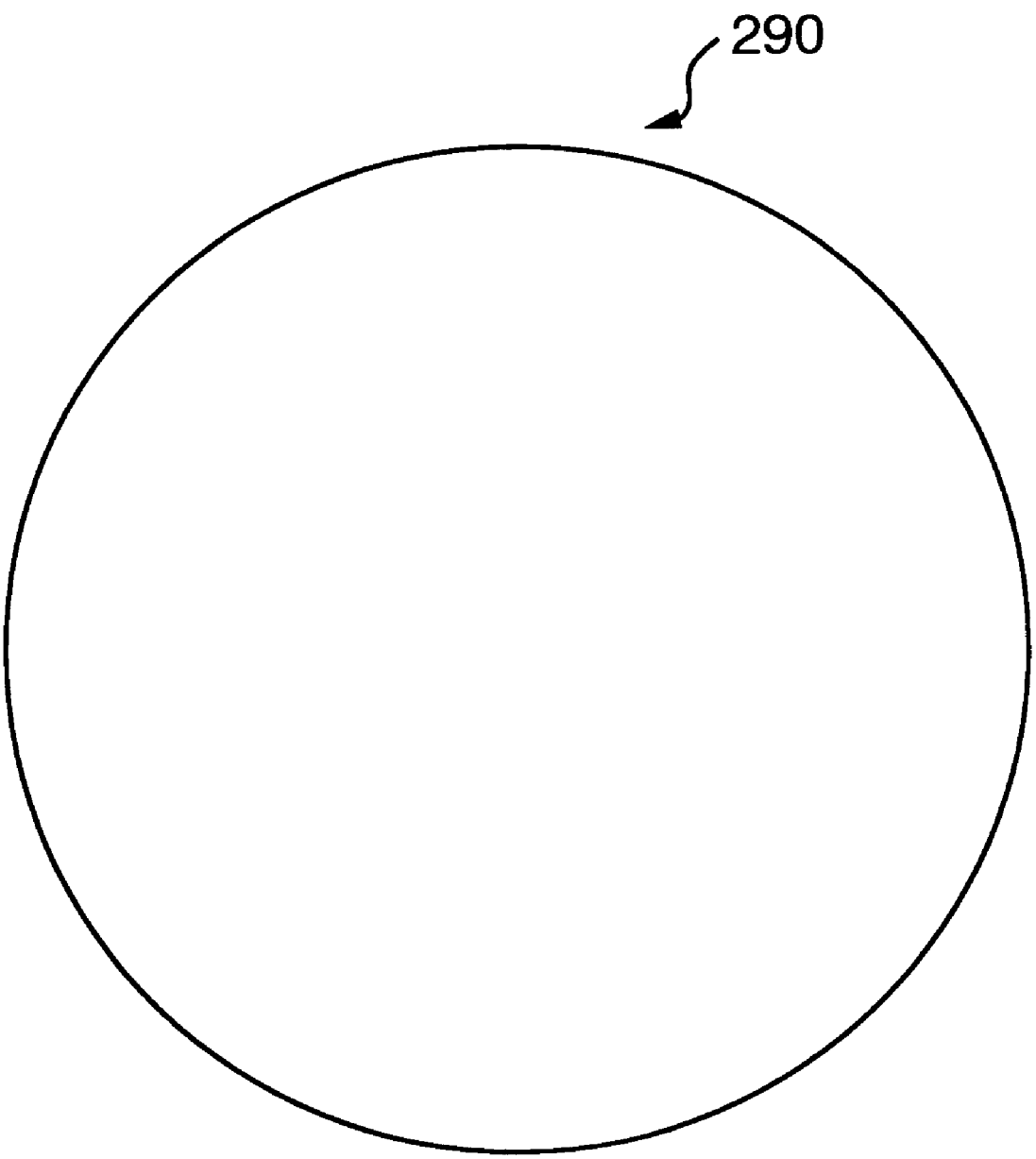
FIG. 9 illustrates yet another alternative keratoscope pattern for use with the present invention.

In a further alternate embodiment, a circular pattern 290 may be utilized to allow calculation of corneal curvature in the perpendicular directions in a normal cornea (FIG. 9). This permits the invention to perform ophthalmometry.

PERIMETER

In addition to being useful for evaluating corneal topography, the present invention may also be utilized as a visual field measuring device, or a perimeter. Perimetry is an integral part of general ophthalmic and optometric practice, primarily as an aid to assessing glaucoma, but also to assess maculopathies and optic neuropathies. Typically, the visual field of a patient was evaluated by having the patient view a background, for example, a projection screen or a CRT, that spans a portion of the patient's visual field.

Figure 10:
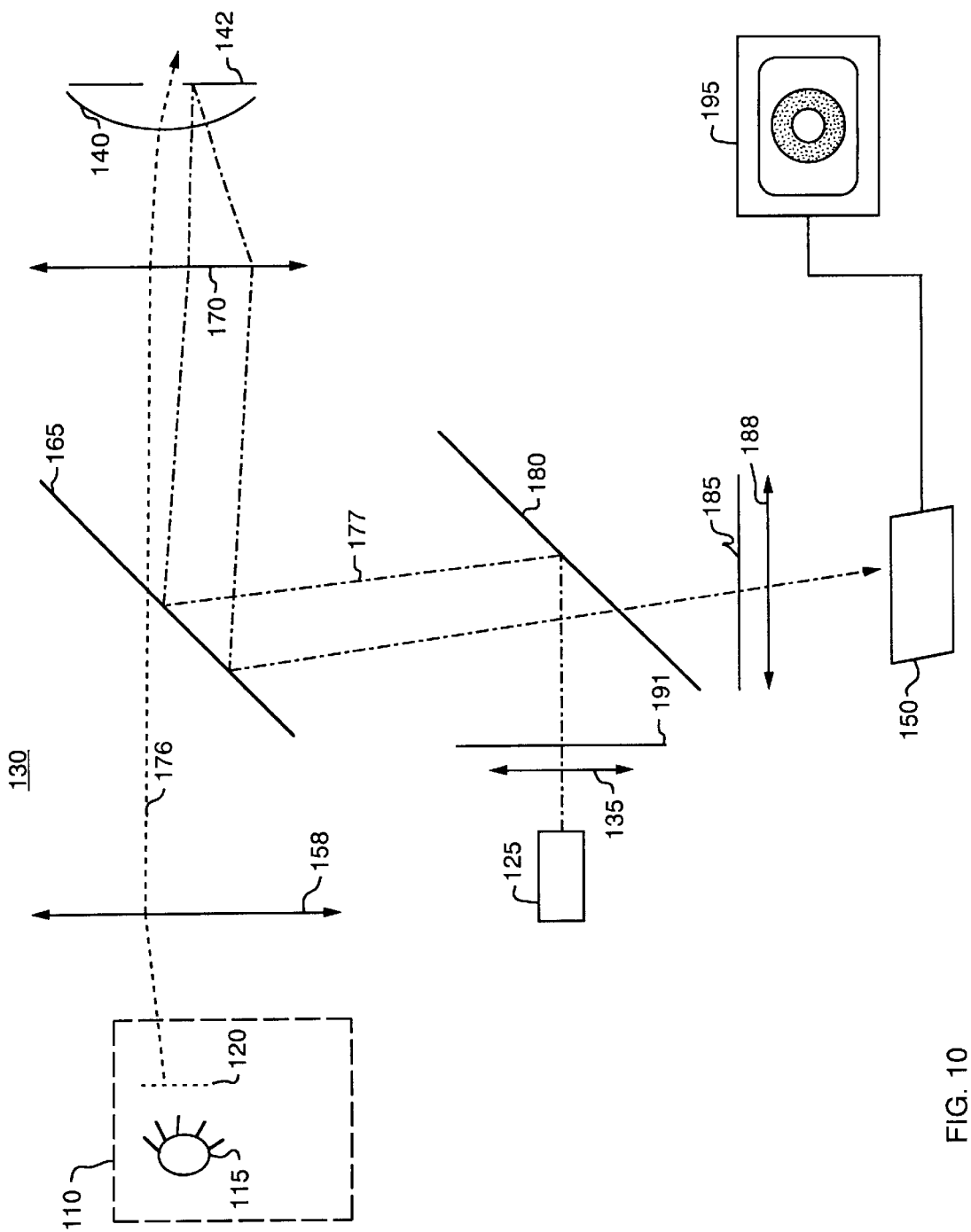
FIG. 10 illustrates the corneal topography device of FIG. 4 reconfigured as a perimeter to measure a patient's visual field.

In order to measure a patient's visual field, the optical system of FIG. 4 is preferably reconfigured as shown in FIG. 10. The structured light source 110 is preferably embodied as a liquid crystal display (LCD), a thin film transistor (TFT) LCD display, a CRT or an array of LEDs, to achieve a moving and changeable fixation target, or other active matrix display. As indicated by light ray 176, the pattern created by structured light source 110 is captured by focusing lens 158 and directed through beam splitter 165 and objective lens 170. The objective lens 170 creates a virtual image of the pattern produced by structured light source 110 that is projected at a preferred distance of 1 meter from the patient's cornea, and spans at least 25° of the patient's visual field. During measurement of the patient's visual field, the patient observes the visual stimulus, namely, the virtual image of video display 120, by viewing through objective lens 170.

To measure the patient's visual field, centration illumination source 125 is preferably embodied as an infrared laser and illuminates the patient's pupil with an infrared beam 177 through a polarizing filter 191 and reflected off two beam splitters 180, 165. Infrared beam 177 is scattered off the patient's iris, is captured by objective lens 170, is reflected off beam splitter 165, transmitted through beam splitter 180, through a polarizing filter 185 and focusing lens 188 and imaged upon CCD chip 150, for display on the screen of computer 195. Polarizing filter 185 is oriented perpendicular to polarizing filter 191, so that scattered light from the patient's iris is preferentially transmitted, and reflected light from the cornea is preferentially blocked.

In operation, the device is centered relative to the patient's pupil, by centering the video image of the pupil. The system monitors fixation by tracking the movement of the patient's pupil, using the scattered infrared image. When the center of the pupil image moves beyond a predefined threshold, an alarm may be activated to indicate when fixation is lost. Preferably, beam modulating system 120 projects a white on gray target of varying size or luminosity to determine threshold sensitivity at each point. Targets of varying luminosity are possible by adjusting the ratio of pixels in the "on" and "off" mode that make up each image.

To calculate the position of the pupil in real time, a weighted threshold algorithm is preferably utilized. Initially, the image intensity of all points in the video image is inverted, so that light pixels become dark, and vice versa. This creates a bright pupil on a dark background. Thereafter, all points in the video image with luminance below a predefined threshold are excluded, because they presumably represent iris points. Finally, the unweighted vector center of the remaining points is calculated, representative of the pupillary center.

In an alternate embodiment, illumination source 125 is aligned with the patient's visual axis so that a bright image of the pupil appears by reflection from the retina of light from illumination source 125. In this case, thresholding can be performed without inverting the pixel intensities, and the unweighted vector center calculated.

In the above embodiments, a virtual image of the keratoscope pattern appears to be located about 30 cm in front of the patient's eye. Such a configuration simulates the function of the keratoscope pattern used in most prior art systems. As discussed above herein, this virtual image is directed to and reflected off the patient's cornea, with distortions in the cornea observed in the reflected image. For some applications, however, it has been found preferable to position the keratoscope pattern at some other location. Although departing from the conventional wisdom, it has been discovered that doing so reduces the complexity and enhances the efficiency of the optical system.

Figure 11:
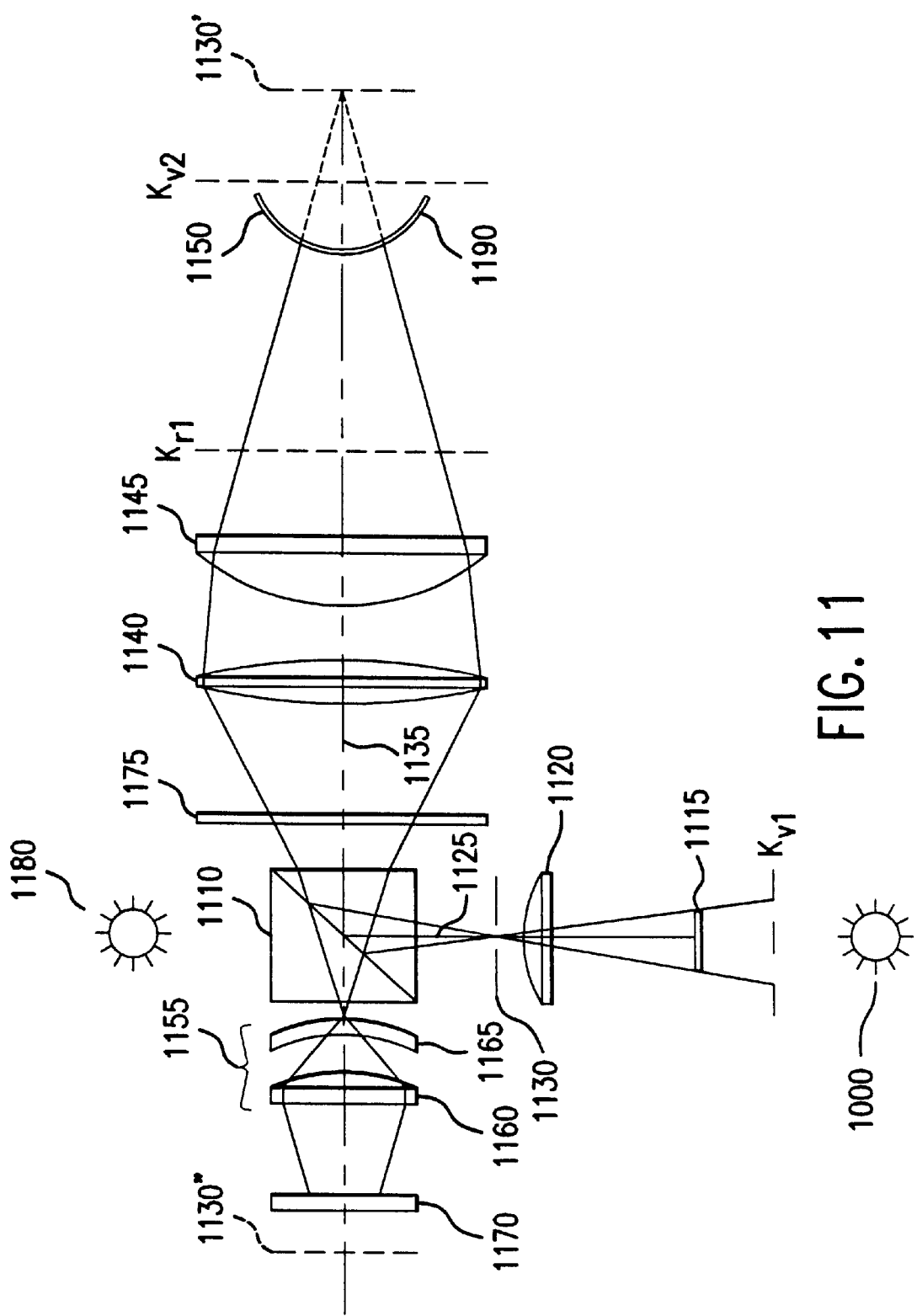
FIG. 11 is a block diagram of another embodiment of a corneal topography device incorporating features of the present invention.

Shown in FIG. 11 is another embodiment of the present invention which is similar to the above embodiments, except that the image of the keratoscope pattern is notably formed at a position not visible as an image to the patient's eye. Contrastingly, in this latter embodiment, a virtual object of the keratoscope pattern is formed just behind the cornea such that after being reflected from the surface of the cornea is re-imaged just in front thereof. Likewise, however, distortions in the cornea are observed in the reflected real image of the keratoscope pattern, which image is then directed onto a CCD, converted into an electrical signal and analyzed by a computer.

Referring to this later embodiment depicted in FIG. 11, a beam splitter 1110 is used to direct to the patient's cornea a virtual image of a keratoscope pattern, $K_{v1}$. Preferably, this keratoscope pattern is created by illuminating a keratoscope target 1115, positioned preferably 4.4 mm inside the front focal plane of a focusing lens 1120, (f=9.5 mm). Alternatively, however, the keratoscope target may be positioned at $K_{v1}$, but would of course lengthen the optical axis of the system. Incoming light rays emanating from keratoscope target 1115 along an optical axis 1125 pass through an aperture stop 1130 approximately 0.3 mm in diameter, strike the reflective surface of beam splitter 1110, and then are directed laterally along an optical axis 1135 through aspheric lenses 1140, 1145 onto the surface of a patient's cornea 1150. Preferably, lens 1140 has a focal length of about 74 mm whereas lens 1145 has a focal length of about 46 mm. If desired, beam splitter 1110 may be mounted such that its angle of rotation is adjustable. In the event that the beam splitter becomes misaligned, realignment is then readily possible. Also, pelicles may be used instead of beam splitters.

A virtual object of the keratoscope pattern $K_{v2}$ is formed approximately 2.8 mm behind the cornea, with the reflected light therefrom forming an image of a keratoscope pattern $K_{r1}$, approximately 10.6 mm in front of the cornea (base radius of curvature of 7.8 mm). It is this latter real image that is distorted by any abnormal shape in the cornea. Lenses 1140, 1145 direct the distorted image of the keratoscope pattern, $K_{r1}$, through optical assembly 1155, consisting of lens 1160 (~f=27 mm) and lens 1165 (~f=6 mm), which are separated apart ~2.8 mm. This optical assembly then focuses the distorted keratoscope pattern image, $K_{r1}$, onto a charge coupled device (CCD) 1170, converting the image into a video signal for image processing, such as by a computer. CCD 1170 is positioned about 2.5 mm behind lens 1160.

As in the previous embodiment, it should be clearly understood that lenses 1140 and 1145 are specifically designed such that the chief rays from keratoscope target 1115 strike the cornea at an angle substantially perpendicular to the surface thereof. Optical analysis and ray tracing indicate this condition specifically also images aperture stop 1130 near or about the nominal center of curvature of the cornea, which may be approximated as an ellipse having a base radius of 7.8 mm and a conic constant of about 0.25. This latter image of aperture stop 1130 is shown as 1130' in the figure. By imposing this condition and also sufficiently limiting the size of the aperture stop, any light rays reflected from the cornea travel substantially along a path parallel or collinear with the corresponding incident light rays. Preferably, the optical system has a working f-number of approximately 360.

This embodiment also uses a unique method of accommodating a wide range of eyes or measuring abnormal corneas. Eyes suffering from keratoconus typically have a small radius of curvature near the center of the cornea, for example, as short as 4 mm. On the other hand, post-refractive surgery eyes may have a radius of curvature as large as 11 mm. Unfortunately, this variation in the radius of curvature shifts the nominal image plane of the keratoscope pattern as well as the image plane of the exit pupil. And, uncorrected may result in an unacceptable image quality. Sufficiently limiting the size of the aperture stop of the optical system, however, compensates for the former inasmuch as it extends the depth of field such that the image remains acceptable, even though the image plane shifts greatly.

Figure 12:
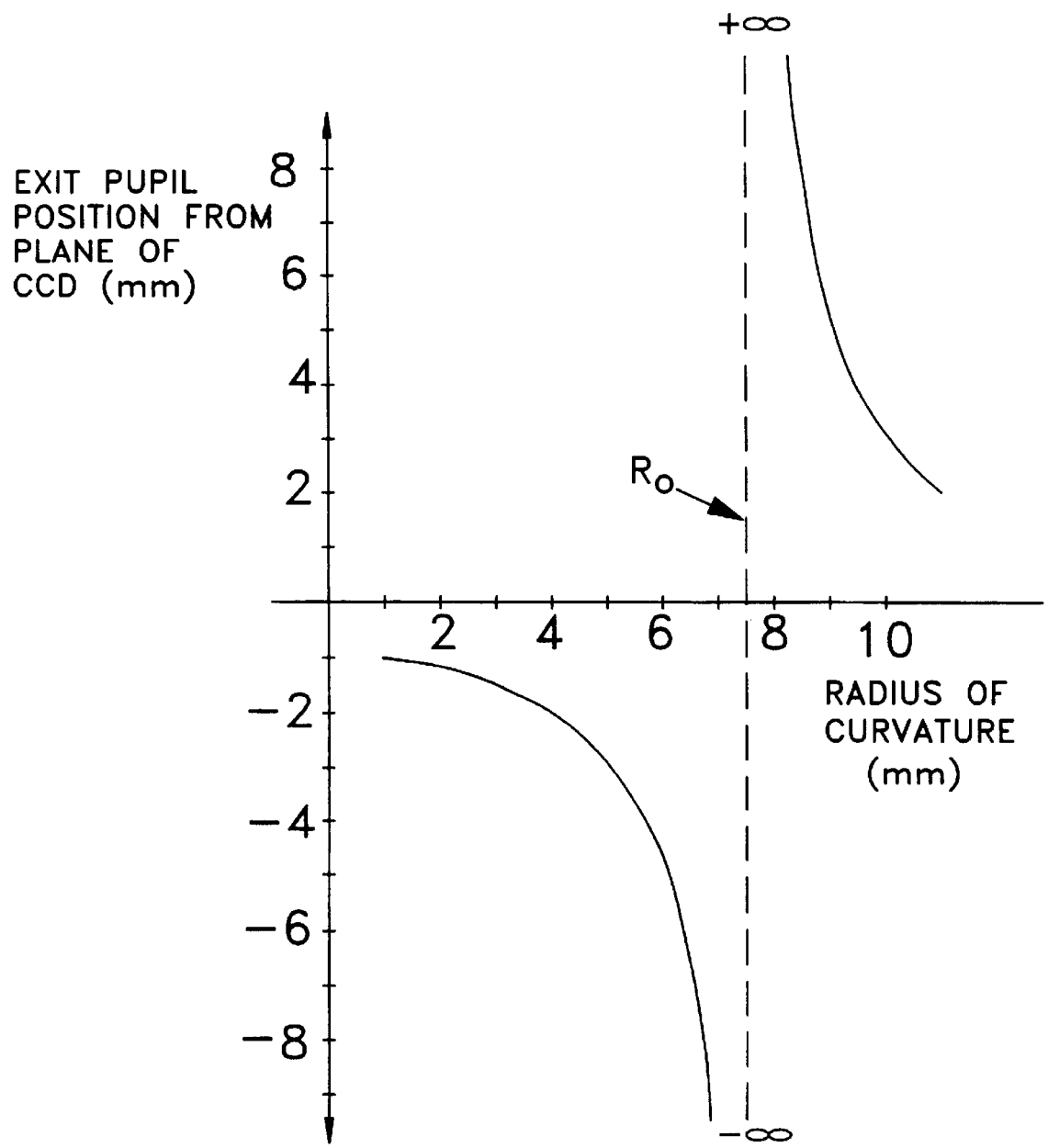
FIG. 12 is a graph showing the location of the exit pupil in the device of FIG. 11 as a function of the base radius of curvature of the cornea.

With regard to the exit pupil, it has been determined that allowing the location of the exit plane to move through the plane of the CCD prohibitively degenerates the image quality. To compensate for this, it has been found that restricting the exit pupil to pass through infinity provides an acceptable image, even for wide variations in the shape of the cornea. In order to better understand this condition, an illustrative graph of the position of the exit pupil (from the nominal image plane) as a function of the base radius of curvature of the cornea is shown in FIG. 12. It should be clearly understood that the nominal image plane is where the image of the reflected keratoscope pattern is formed for a normal cornea and herein coincident with the plane of the CCD.

First, consider a cornea having a short base radius of curvature of 4 mm. In this latter instance, exit pupil 1130" is located a short distance (~2.1 mm) in front of the plane of the CCD. As the radius of curvature approaches the limiting radius $R_o$, the location of exit pupil 1130" approaches negative infinity. And, further increasing the radius of curvature shifts the location of the exit pupil toward the plane of the CCD, but does so from positive infinity, as illustrated. For a normal cornea having a base radius of curvature of 7.8 mm, exit pupil 1130" is located about 26.4 mm behind the plane of the CCD.

In general, the location of the exit pupil satisfies approximately the following equation:

$$L = \frac{C_1}{(R_o - r)}$$

wherein L is the distance of the exit pupil from the plane of the CCD; $R_o$ is 7.51 and $C_1$ is −7.55; and r is the base radius of curvature of the cornea.

Thus, it has been found that an optical system as described above herein is well suited to compensate for variations in the radius of curvature inasmuch as the location of the exit pupil never passes through the plane of the CCD. This is so even though the location of the exit pupil shifts from one side of the plane of the CCD to the other.

In the previous embodiments discussed above herein, fixation was readily achieved by having the patient look at the center of the keratoscope pattern and as such along the optical axis of the instrument. It should be recalled, however, that in the present embodiment the keratoscope pattern is not visible to the patient's eye, other than as an overall illumination. This is so because the keratoscope pattern is focused to a point located just behind the patient's cornea. Accordingly, in this embodiment a separate visible fixation pattern is provided to ensure that the patient's visual axis is aligned with the optical axis of the instrument. More specifically, a fixation target 1175 consisting of a clear glass plate with a small black pattern is positioned within the back focal plane of the lens system formed by lenses 1140 and 1145. In this manner, a virtual fixation pattern can be formed at a distance of about 40 cm in front of the patient's eye. Of course, the features within the fixation target are judiciously chosen to be large enough for the patient to focus on (~5–10 arc minutes) when viewing the pattern, but small enough not to block the light rays reflected from the cornea.

Similarly, pupil detection may be accomplished using on-axis illumination as described herein above for the previous embodiments. Likewise, focusing may be accomplished using a portion of a beam scattered or reflected off the cornea, as described herein above. It is contemplated, however, that off-axis illumination may also be used for pupil detection. Referring back to FIG. 11, lenses 1140 and 1145 may be used to image an off-axis illumination source 1180 to the patient's iris. Radiation scattered from the iris is likewise collected and imaged onto CCD 1170 so as to detect and locate the edge of the pupil in a manner described above herein. Off-axis illumination may even be preferable since it prevents specular reflections from the cornea and retina from interfering with locating the edge of the pupil.

In accordance with another aspect of the present invention, the present invention may also be readily used as an ophthalmic instrument for imaging disruptions or abnormalities in the eye's tear film. The tear film is a clear multi-layer fluid secreted by the tear glands which coats the front of the cornea. Corneal topographers, including the optical system of the present invention, actually measures the shape of the outer surface of the tear film, and not the cornea itself. Surface tension, however, normally, causes the tear film to be uniformly thick over the entire cornea so that the shape of the outer surface of the tear film accurately represents the shape of the underlying cornea. Accordingly, it should be understood that it is the outer surface of the tear film that is being referred to when discussing the imaging of the cornea.

Figure 13:
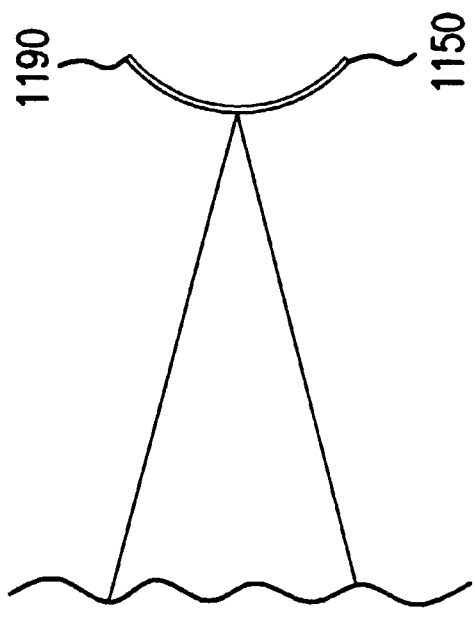
FIG. 13 is an enlarged view of the location of the aperture stop in existing corneal topographers useful in understanding the capability of the present corneal topography device to visualize abnormalities in the eye's tear film.
Figure 13:
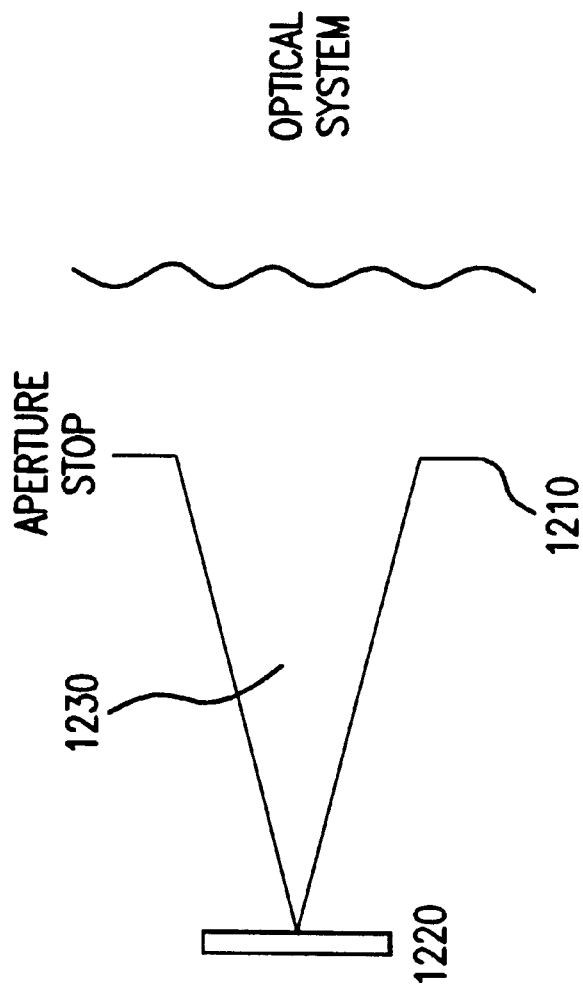

When the tear film, however, becomes contaminated, when its production becomes limited, or when its chemical composition varies, the tear film becomes disrupted due to its varying thickness, which is typically an indication of a disease or other physiological problem. As such, an aid to the diagnosis of eye diseases is examining the tear film for such disruptions or abnormalities. Typically, various dyes are used to make the tear film visible for examination with a biomicroscope. In certain instances, however, dyes cannot be used in sufficient concentration to observe the tear film. Moreover, certain dyes are painful when introduced into the eye. Moreover, in prior art corneal topographers, local disruptions in the tear film may sometimes appear as slight discontinuities in the "mires." These discontinuities, however, are very difficult to see, if at all, and normally appear neither in the captured image nor in the processed surface contour of the cornea. As shown in FIG. 13, in existing corneal topographers, the aperture stop 1210 of the optical system is located somewhere along the optical axis of the collection optics between the eye and a detector 1220 upon which light reflected from tear film 1190 is detected. It has been recognized, however, that in such a design the f-number of the cone of light 1230 incident on detector 1220 is constant, independent of the corneal curvature. Inasmuch as the image intensity is inversely proportional to the square of the f-number, a fixed f-number necessarily equates to an image intensity that is independent of the shape of the corneal surface, making disruptions in the tear film extremely difficult to observe due to a lack of contrast.

Advantageously, the present invention may also be employed to readily visualize disruptions or abnormalities in the eye's tear film by observing localized changes in the intensity of the reflected light from the corneal surface and, more precisely, from the outer surface of tear film 1190, as discussed herein above. For example, small air or oil bubbles appear as "black spots" in the acquired corneal image, whereas localized changes in thickness that occur, for example, after blinking appear as parallel bright lines. This latter embodiment of the present invention is similar to that of FIG. 11, except that it is preferable not to use the keratoscope pattern which could obscure localized intensity variations. Similarly, the illumination is directed substantially normal to the surface of cornea 1150 or tear film 1190, with the reflected light then directed onto CCD 1170 so as to form an image of the outer surface of tear film 1190, indicative of the shape of cornea 1150. This reflected light illuminates CCD 1170 such that localized intensity variations are indicative of discontinuities in the tear film, as discussed herein below. Such intensity variations, for the first time, make tear film anomalies readily visible. And, to a trained ophthalmologist, the acquired image of the cornea, including disruptions in the tear film, when compared with those of healthy and diseased eyes, or of the same eye during medical treatment, provides information upon which a diagnosis can be made.

Referring again to FIG. 11, beam splitter 1110 is used to direct illumination to cornea 1150 or precisely to tear film 1190 from a light source 1000, which may include a diffuser to approximate a Lambertian source. Alternatively, an image of keratoscope target 1115 may be directed to the cornea, as discussed herein above. The radiation emitted from light source 1000 may be in the non-visible range, which would minimize any discomfort caused by high intensity illumination. The spectral characteristics of the illumination, of course, may be tailored to the desired application by judiciously selecting the spectral characteristics of light source 1000, including the visible and infrared spectrum region.

Likewise, incoming light rays emanating from light source 1000 along optical axis 1125 pass through aperture stop 1130 approximately 0.3 mm in diameter, strike the reflective surface of beam splitter 1110 and then are directed laterally along optical axis 1135 though aspheric lenses 1140, 1145 to cornea 1150, the light being reflected off the outer surface of the tear film. Alternatively, rays emanating from keratoscope pattern 1115 are directed to the cornea. Although aperture stop 1130 is judiciously located along the optical axis of the illumination optics at a position before the incoming illumination reaches the eye, there is no aperture stop along optical axis of the collection optics, i.e., optical axis 1135. In doing so, the total light reaching the eye and reflected into the collection optics (lenses 1140, 1145, and 1155) is constant (not the intensity), and thus independent of the shape of the corneal surface. This may be better understood by observing that the f-number of the cone of light directed to the eye is constant since the solid angle subtended by aperture stop 1130 with respect to cornea 1150 is fixed. With the illumination inversely proportional to the square of the f-number, the illumination reaching the eye and then reflected off the cornea is constant and independent of the shape of the cornea. As the corneal surface changes shape, the size of the corneal image on CCD 1170, however, correspondingly changes. A flatter corneal surface has less magnification, producing a smaller image than a more curved corneal surface which conversely produces a larger image. Now since the total light reflected from the outer surface of the tear film is constant due to the positioning of aperture stop 1130, a smaller image with the same amount of light therein produces a brighter image than a larger image, which produces a dimmer image.

Preferably, aperture stop 1130 is located within the optical system of the corneal topographer such that a virtual object 1130' of aperture stop 1130 is located near or about the nominal center of curvature of cornea 1150. In this manner, chief rays from light source 1000 strike the outer surface of tear film 1190 at an angle substantially normal to the outer surface thereof.

The above same effect, of course, applies when imaging local variations in curvature of cornea 1150 caused by variations in the thickness of tear film 1190. That is, localized changes in the curvature of the cornea caused by abnormalities in the tear film correspondingly changes the magnification. Flatter surfaces produce a smaller image magnification, but one which is brighter. Thus, localized changes in the thickness of tear film 1190 are visualized through changes in the localized intensity of the acquired image of the cornea formed on CCD 1170. Less curvature results in a brighter image, whereas more curvature results in a dimmer image. Note that when a keratoscope pattern is employed, this effect produces local discontinuities in the mires.

It should be understood, however, that the localized intensity of the corneal image is only a function of the curvature so long as the reflected light from tear film 1190 does not exceed a certain threshold angle. Otherwise, the reflected light does not reach CCD 1170 due to the limited size of collecting lenses 1140, 1145, and 1155, causing the image to go dark. This occurs for extreme changes in curvature, such as when there are bubbles or contaminations in the tear film.

It is to be also understood that the embodiments and variations shown and described herein are illustrative of the principles of this invention only and that various modifications may be implemented by those skilled in the art without departing from the scope and spirit of the invention.

What is claimed is:

1. An ophthalmic instrument for imaging an eye's tear film which covers the cornea, said ophthalmic instrument comprising:

an illumination source;

means for directing along an illumination optical axis illumination to the outer surface of said tear film, wherein the aperture stop of the ophthalmic instrument is located along the illumination optical axis before the illumination reaches the tear film such that the illumination reaching the tear film is substantially independent of the shape of the tear film;

an imaging sensor;

means for directing along a collection optical axis the light reflected from the outer surface of the tear film onto said imaging sensor, whereby disruptions in the tear film are observed as localized intensity variations due to changes in image magnification resulting from corresponding thickness variations in the tear film.

2. The ophthalmic instrument of claim 1 wherein said illumination source includes a keratoscope pattern.

3. The ophthalmic instrument of claim 1 wherein a virtual object of the aperture stop is located near or about the nominal center of curvature of the cornea.

4. The ophthalmic instrument of claim 1 wherein the aperture stop is positioned in a manner such that the chief rays from the illumination source strike the tear film at an angle substantially normal to the outer surface thereof.

5. The ophthalmic instrument of claim 1 wherein flatter portions of the outer surface of the tear film produces a smaller, but brighter image magnification than portions having a greater curvature.

6. The ophthalmic instrument of claim 1 wherein said illumination source is a Lambertian source.

7. The ophthalmic instrument of claim 1 wherein said imaging sensor is a CCD.

8. The ophthalmic instrument of claim 1 wherein said illumination source includes a laser.

9. The ophthalmic instrument of claim 1 wherein said illumination source includes a LED.

10. The ophthalmic instrument of claim 1 wherein said illumination source emits radiation in the visible spectrum.

11. The ophthalmic instrument of claim 1 wherein said illumination source emits radiation in the infrared spectrum.

12. An ophthalmic instrument for imaging an eye's tear film which covers the cornea, said ophthalmic instrument comprising:

a light source;

an imaging sensor;

an optical lens system having an aperture stop;

a beam splitter for directing along an illumination optical axis illumination through said optical lens system which focuses the illumination to a point behind the cornea, and also forms a virtual object of said aperture stop at or near the nominal center of curvature of said cornea, said optical lens system collecting along a collection optical axis light reflected from the outer surface of the tear film and passing the reflected light to said beam splitter which focuses said reflected light onto said imaging sensor, whereby disruptions in the tear film are observed as localized intensity variations due to changes in image magnification resulting from corresponding thickness variations in the tear film.

13. The ophthalmic instrument of claim 12 wherein said light source includes a keratoscope pattern.

14. The ophthalmic instrument of claim 12 wherein the chief rays from the light source strike the tear film at an angle substantially normal to the outer surface thereof.

15. The ophthalmic instrument of claim 12 wherein flatter portions of the outer surface of the tear film produces a smaller, but brighter image magnification than portions having a greater curvature.

16. The ophthalmic instrument of claim 12 wherein said light source is a Lambertian source.

17. The ophthalmic instrument of claim 12 wherein said imaging sensor is a CCD.

18. The ophthalmic instrument of claim 12 wherein said light source includes a laser.

19. The ophthalmic instrument of claim 12 wherein said light source includes a LED.

20. The ophthalmic instrument of claim 12 wherein said light source emits radiation in the visible spectrum.

21. The ophthalmic instrument of claim 12 wherein said light source emits radiation in the infrared spectrum.

\* \* \* \* \*